US00PP12707P2

(12) United States Plant Patent

Olesen et al.

(10) Patent No.: US PP12,707 P2

(45) Date of Patent: Jun. 18, 2002

(54) ROSE PLANT NAMED 'POULTIEME'

(76) Inventors: L. Pernille Olesen; Mogens N. Olesen, both of Hillerødvejen 49, DK-3480 Fredensborg (DK)

( * ) Notice: Subject to any disclaimer, the term of this patent is extended or adjusted under 35 U.S.C. 154(b) by 0 days.

(21) Appl. No.: 09/276,893

(22) Filed: Mar. 25, 1999

(51) Int. Cl.[7] ..... A01H 5/00

(52) U.S. Cl. ..... Plt./109

(58) Field of Search ..... Plt./109, 114, 115

(56) References Cited

PUBLICATIONS

Copy of EU 6842, granted Nov. 6, 2000 and EU 97/0131 filed Jan. 27, 1997.*

UPOV–ROM, 2001/01, Plant Variety Database, GTI Jouve Retrieval Software, citation for 'POULtieme'.*

UPOV–ROM, 2000/05, Plant Variety database, GTI Jouve Retrieval Software, citation for 'POULtime'.*

* cited by examiner

*Primary Examiner*—Howard J. Locker

(57) ABSTRACT

A new garden rose plant which has abundant, dark pink flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between 'Morning Jewel' and an unnamed seedling. The two parents were crossed and the resulting seeds were planted in a controlled environment. The new variety is named 'POULtieme'.

The new rose may be distinguished from its seed parent, 'Morning Jewel', by the following combination of characteristics:

1. The seed parent has lighter pink blooms when compared to 'POULtieme's' dark pink blooms;
2. The seed parent blooms recurrently, 'POULtieme' also blooms recurrently, but blooms more often during the growing season.

The new variety may be distinguished from its pollen parent, an unnamed seedling created by the same inventors, by the following combination of characteristics:

1. The blooms of the pollen parent are yellow; whereas the blooms of 'POULtieme' are dark pink;
2. The habit of the pollen parent is shrubby; whereas, POULtieme is a climbing rose.

The objective of the hybridization of this rose variety for garden use was to create a new and distinct variety with unique qualities, such as:

1. Uniform and abundant flowers;
2. Vigorous growth;
3. Disease resistance;

This combination of qualities is not present in previously available commercial cultivars of this type and distinguishes 'POULtieme' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULtieme' was selected in the spring 1991 by the inventors as a single plant from the progeny of aforementioned hybridization.

Asexual reproduction of 'POULtieme' by traditional budding was first done by L. Pernille and Mogens N. Olesen in their nursery in Fredensborg, Denmark in August, 1991. This initial and other subsequent propagations conducted in controlled environments have demonstrated that the characteristics of 'POULtieme' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves and stems of 'POULtieme'. Specifically illustrated in SHEET 1:

1. Stem of the plant showing branching and the attachment of leaves, buds, and peduncles;
2. Flower bud, partially opened bud, and open bloom;
3. Flower petals, detached;
4. Sepals, receptacle, and pedicel;
5. A bare stem exhibiting thorns;
6. Leaves.

DETAILED DESCRIPTION OF THE VARIETY

The following is a description of 'POULtieme', as observed in its outdoor growth in a field nursery in Jackson County, Oreg. Observations were conducted during September, 1998. Color references are made using The Royal Horticultural Society (London, England) Colour Chart, 1995, except where common terms of color are used.

For a comparison, several physical characteristics of the rose variety 'POULclimb', a climbing rose variety, from the same inventors, described and illustrated in U.S. Plant Pat. No. 10,639 and issued on Oct. 13, 1998 are compared to 'POULtieme' in Chart 1.

CHART 1

| | 'POULtieme' | 'POULclimb' |
|---|---|---|
| Bloom color when fully open. | Red-Purple Group 58C on upper surface and Red-Purple 65C on reverse side. | Irregularly striped with colors as dark as 64D-60D and as light as 155D-11D. |
| Petalage. | Semi-double; 12–14 petals. | Semi-double; 10–15 petals. |
| Growth. | Climbing habit, arching canes, 200–250 cm. in length. | Climbing habit, very vigorous, long canes, 300–350 cm in length. |

Parents:
*Seed parent.*—'Morning Jewel'.
*Pollen parent.*—Unnamed seedling.
Classification:
*Botanical.*—*Rosa hybrida.*
*Commercial.*—Climber.

FLOWER AND FLOWER BUD

Blooming habit: Recurrent.
Flower bud:
*Size.*—Upon opening, 25 mm–30 mm in length from base of receptacle to end of bud.
*Bud form.*—Short, pointed ovoid to globular.
*Bud color.*—As sepals unfold, Red-Purple Group 58B to Red Group 54A. Red-Purple Group 58C–58D at ¼ opening.
*Sepals.*—Green Group 144B. Weak foliaceous appendages on three of the five sepals. Surfaces of sepals slightly pubescent. Stipitate glands are present in limited numbers on margins.
*Receptacle.*—Surface: Smooth, glabrous. Shape: Pear to urn-shaped. Size: Medium. 6 mm (h)×6–7 mm (w). Color: Green Group 137A.
*Peduncle.*—Surface: Smooth, with moderate numbers of stipitate glands. Length: 40–50 mm average length. Color: Yellow-Green Group 144B, with intonation of Greyed-Red Group 180A. Strength: Upright.
*Borne.*—Multiple buds per stem typically with 2–4 buds per flowering stem.
Flower bloom:
*Fragrance.*—Light floral fragrance.
*Duration.*—The blooms have a duration on the plant of approximately 3 to 6 days. Petals fall cleanly away from plant.
*Size.*—Average flower diameter is 65–70 mm when open.
*Form.*—Shape of flower when viewed from the side: Upon opening, upper part: Convex. Upon opening, lower part: Convex. Open flower, upper part: Flattened convex. Open flower, lower part: Flat.
*Petalage.*—Semi-double. Average range: 12–14 petals under normal conditions with 2–4 petaloids.
Color:
*Upon opening, petals.*—Upper Surface: Red-Purple Group 57A–Red Group 46D. Reverse Side: Red Group 52A–52B.
*Upon opening, basal petal spots.*—Outer Side: Green-Yellow Group 1B. Inner Side: Green-Yellow Group 1A.
*After opening, petals.*—Upper Surface: Red-Purple Group 58C. Reverse Side: Red-Purple Group 65C.
*After opening, basal petal spots.*—Outer Side: Green-Yellow Group 1D to Green-White Group 157D. Inner Side: Green-Yellow Group 1D.
General tonality: Open flower is Red-Purple Group 58C. No change in the general tonality at the end of the third day. Afterwards, general tonality is Red-Purple Group 60D.
Petals:
*Petal reflex.*—On open flower, almost all petals are double reflexed.
*Petal edge.*—Somewhat ruffled.
*Shape.*—Round.
*Petaloids.*—2–4 petaloids.
*Thickness.*—Average.
*Arrangement.*—Informal.
Reproductive organs:
*Pollen.*—Color: Yellow-Orange Group 15C. Quantity: Limited.
*Anthers.*—Size: Large. Color: Immature: Yellow-Orange Group 14C. Mature: Greyed-Orange Group 164C and Brown Group 200B. Quantity: Abundant.
*Filaments.*—Color: Green-Yellow Group 1A.
*Stigmas.*—Numbers of female floral parts very limited. Stigmas are inferior in location to anthers. Color: Yellow-Green Group 145D.
*Styles.*—Color: Green-White Group 157A. Texture: With fine white hairs.
*Hips.*—None observed.

PLANT

Plant growth: Climbing habit, vigorous, upright to arching canes with canes reaching a height of 200–250 cm.
Stems:
*Color.*—Young wood: Yellow-Green Group 144C. Older wood: Yellow-Green Group 144C.
*Thorns.*—Incidence: Few to moderate. Size: Average length: 7 mm. Color: Yellow-Green Group 145C with slight intonations of Red Group 39D. Shape: Nearly linear with downward slant.
*Surface.*—Young wood: Smooth. Older wood: Smooth.
Plant foliage: Normal number of leaflets on leaves in middle of the stem: 5 leaflets.
*Leaf size.*—Small to medium. 120–130 mm (1)× 90–100 mm (w).
*Quantity.*—Average.
*Color.*—Upper Leaf Surface: Green Group 137A to Yellow-Green Group 147A. Lower Leaf Surface: Yellow-Green Group 147C. Anthocyanin: None observed.
*Juvenile foliage.*—Upper Leaf Surface: Green Group 137A. Lower Leaf Surface: Yellow-Green Group 147 C. Anthocyanin: None observed.
*Stipules.*—Size: 15 mm–20 mm. Color: Yellow-Green Group 146B. Stipitate glands: Limited numbers on margins.
*Petiole.*—Length: 24 mm–28 mm. Color: Yellow-Green Group 146C–146D. Underneath: Smooth. Margins: Smooth, few to no stipitate glands or hairs.
*Rachis.*—Color: Yellow-Green Group 146C–146D. Underneath: Smooth. Only 1–2 small prickles on rachis. Margins: Smooth.
*Leaflet.*—Edge: Serrated. Shape: Ovate. Texture: Moderately glossy and leathery.

Disease resistance: Above average resistance to mildew, rust, and black spot under normal growing conditions in Jackson County, Oreg.

Cold hardiness:

POULtieme has been found to be cold hardy in Denmark and in Jackson County, Oreg.

We claim:

1. A new and distinct variety of rose plant of the climbing class, substantially as herein illustrated and described as a distinct and novel rose variety due to its abundant, dark pink flowers, vigorous growth, climbing habit and disease resistance.

* * * * *

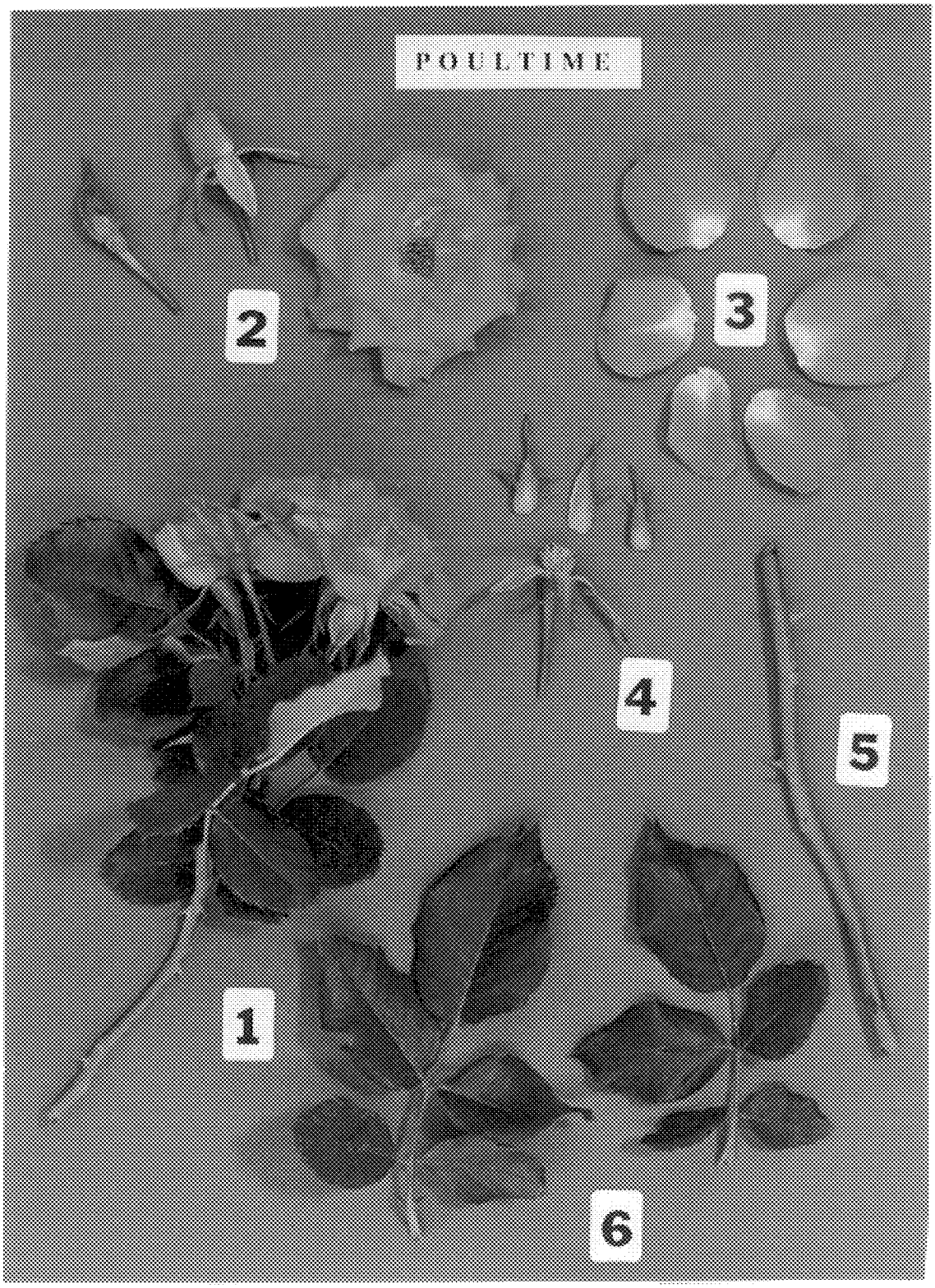
POULTIME
2
3
4
5
1
6